(12) United States Patent
Freer et al.

(10) Patent No.: US 8,209,004 B2
(45) Date of Patent: Jun. 26, 2012

(54) BODY-BASED MONITORING OF BRAIN ELECTRICAL ACTIVITY

(75) Inventors: Peter A. Freer, Skyland, NC (US); Stephen J. Scanzoni, Asheville, NC (US); Randall S. Nuss, Asheville, NC (US)

(73) Assignee: Freer Logic, LLC, Skyland, NC (US)

( * ) Notice: Subject to any disclaimer, the term of this patent is extended or adjusted under 35 U.S.C. 154(b) by 910 days.

(21) Appl. No.: 12/144,265

(22) Filed: Jun. 23, 2008

(65) Prior Publication Data
US 2009/0318827 A1    Dec. 24, 2009

(51) Int. Cl.
*A61B 5/0476* (2006.01)
*A61B 5/0478* (2006.01)

(52) U.S. Cl. ......... 600/544; 600/373; 600/382; 600/546

(58) Field of Classification Search .................. None
See application file for complete search history.

(56) References Cited

U.S. PATENT DOCUMENTS

| | | | |
|---|---|---|---|
| 4,955,388 A | 9/1990 | Silberstein | |
| 5,038,782 A | 8/1991 | Gevins et al. | |
| 5,241,967 A | 9/1993 | Yasushi et al. | |
| 5,740,812 A | 4/1998 | Cowan | |
| 5,983,129 A | 11/1999 | Cowan et al. | |
| 6,097,981 A | 8/2000 | Freer | |
| 6,167,298 A | 12/2000 | Levin | |
| 6,402,520 B1 | 6/2002 | Freer | |
| 6,457,975 B1 | 10/2002 | Miranda et al. | |
| 6,626,676 B2 | 9/2003 | Freer | |
| 6,640,122 B2 | 10/2003 | Manoli et al. | |
| 6,694,180 B1 | 2/2004 | Boesen | |
| 6,795,724 B2 | 9/2004 | Hogan | |
| 6,970,731 B1 | 11/2005 | Jayaraman et al. | |
| 7,173,437 B2 | 2/2007 | Hervieux et al. | |
| 7,181,793 B2 | 2/2007 | Lee | |
| 8,019,402 B1* | 9/2011 | Kryzpow et al. | 600/386 |
| 2002/0029005 A1* | 3/2002 | Levendowski et al. | 600/545 |
| 2002/0188216 A1 | 12/2002 | Kayyali et al. | |
| 2004/0230549 A1 | 11/2004 | Freer et al. | |
| 2005/0096513 A1 | 5/2005 | Ozguz et al. | |
| 2007/0078324 A1 | 4/2007 | Wijisiriwardana | |
| 2007/0249952 A1 | 10/2007 | Rubin et al. | |
| 2008/0027346 A1 | 1/2008 | Litt et al. | |
| 2008/0045808 A1 | 2/2008 | Hassonjee et al. | |
| 2008/0143080 A1 | 6/2008 | Burr | |
| 2008/0177197 A1* | 7/2008 | Lee et al. | 600/545 |

FOREIGN PATENT DOCUMENTS

| | | |
|---|---|---|
| DE | 3921784 A1 | 7/1989 |
| EP | 1 749 477 A1 | 2/2007 |
| WO | 9827864 | 7/1998 |
| WO | 2007139861 A2 | 12/2007 |

OTHER PUBLICATIONS

Ferree et al (Clinical Neurophysiology, 2001, 112:536-544).*
Lin et al (Engin. Psychol. and Ergonomics, HCII 2007, LNAI 4562, p. 561-567).*
International Search Report prepared by the European Patent Office as International Searching Authority in corresponding application PCT/US09/48083 mailed Dec. 23, 2009.

* cited by examiner

*Primary Examiner* — Laura B Goddard
(74) *Attorney, Agent, or Firm* — Carter & Schnedler, P.A.

(57) ABSTRACT

Apparatus and methods for monitoring electrical activity within the brain of a person ("brainwaves") employing electrodes or other sensors connected or placed proximate to portions of the body below the head to develop raw signals. The raw signals are filtered to produce analysis signals including frequency components relevant to brain electrical activity while attenuating unrelated frequency components. Purposes include but are not limited to, biofeedback-based attention training, human performance training, gaming, and relaxation training. Either wired or wireless signal connections are made to electronic circuitry, typically including a digital computer, for performing signal processing and analysis functions.

14 Claims, 12 Drawing Sheets

BODY-BASED MONITORING OF BRAIN ELECTRICAL ACTIVITY

BACKGROUND OF THE INVENTION

The invention relates to the monitoring of electrical activity within the brain of a person for purposes such as, but not limited to, biofeedback-based attention training, human performance training, gaming, and relaxation training.

The term electroencephalography (EEG) is generally employed to refer to the measurement of electrical activity produced by the brain as measured or recorded from electrodes placed on the scalp of a person. Such activity is commonly termed "brainwave" activity. (The related term electroencephalogram refers to a graphic record produced by an electroencephalograph.) The resultant electrical signals from the electrodes are correspondingly termed EEG signals or brainwave signals, and are based on the electrical activity within the brain of a person.

A system for naming points on the scalp or head where EEG electrodes are placed has been developed. Thus, the International "10-20" system is widely used to describe the location of EEG scalp electrodes for standardization. The 10-20 system is based on the surface placement of the electrode and its relationship to the underlying area of cerebral cortex. The "10" and "20" refer to the actual distances between adjacent electrodes as either 10% or 20% of the total front-back or right-left distance of the skull. Further, the letters F, T, C, P and O, which stand for Frontal, Temporal, Central, Parietal and Occipital, respectively, are used to identify the lobe over which the sensor is placed. A number is further used to identify the hemisphere location. Even numbers (2, 4, 6, 8) refer to electrode positions on the right hemisphere, and odd numbers (1, 3, 5, 7) refer to electrode positions on the left hemisphere.

SUMMARY OF THE INVENTION

In one aspect, a method is provided for monitoring EEG electrical activity within the brain of a person having a body including a head. The method includes positioning a sensor at least proximate to portions of the skin of the body below the head (with the exception of the head) to develop raw signals, and filtering the raw signals to produce analysis signals including frequency components relevant to EEG brain electrical activity while attenuating unrelated frequency components.

In another aspect, a method is provided for monitoring a mental state of a person having a body including a head. The method includes positioning a sensor at least proximate to portions of the skin of the body below the head (with the exception of the head) to develop raw signals, and processing the raw signals to produce at least one bandpass-filtered state-indicating signal representative of raw signal magnitude within a predetermined frequency range as an indication of the mental state of the person.

In yet another aspect, a method is provided for monitoring the level of attention of a person having a body including a head. The method includes positioning a sensor at least a pair of sensors at least proximate to portions of the body below the head (with the exception of the head) to develop signals, and analyzing the signals to provide an indication of the person's level of attention by isolating frequency components relevant to brain electrical activity indicative of the person's level of attention while attenuating unrelated frequency components.

In still another aspect, apparatus is provided for monitoring electrical activity within the brain of a person having a body including a head. The apparatus includes a sensor; a unit including at least an amplifier connected for receiving signals from the sensors; a body-attachment device configured for attachment to a portion of the person's body below the head, the body-attachment device providing structural support for the sensor and for the unit, and the body-attachment device positioning the sensor at least proximate to the skin of the body of the person with the exception of the head; and a programmed computing device receiving signals from the amplifier. The unit and the computing device function together to isolate and analyze frequency components of the signals relevant to brain electrical activity while attenuating unrelated frequency components.

DETAILED DESCRIPTION

Figure 1:
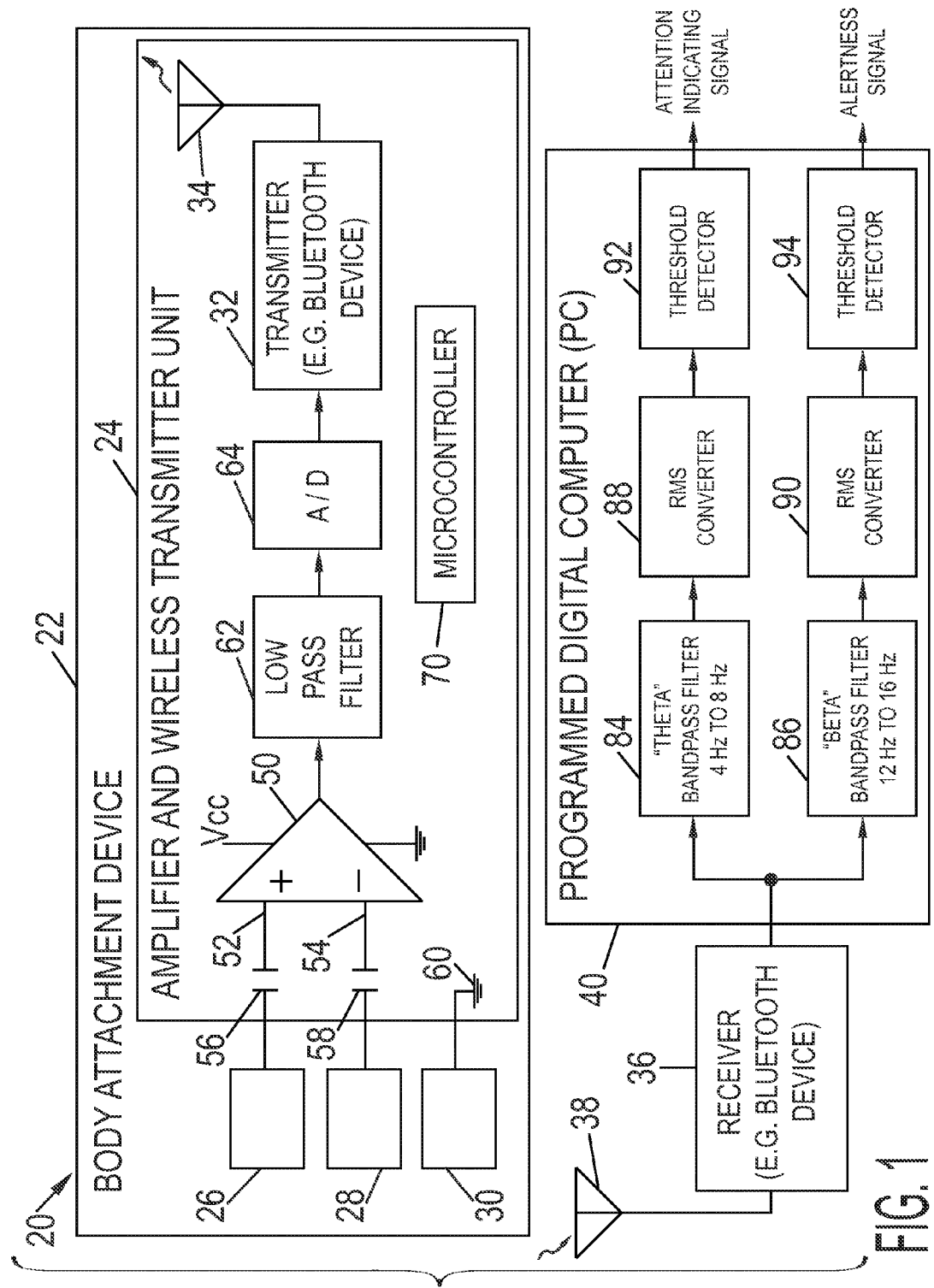
FIG. 1 is a schematic representation of apparatus embodying the invention.

In overview, apparatus and methods for monitoring brainwaves and embodying the invention do not employ electrode attachment to the head, but instead employ electrodes or other sensors connected or placed proximate to portions of the body below the head. Either wired or wireless signal connections are made to electronic circuitry, typically including a digital computer, for performing signal processing and analysis functions. One topology embodying the invention employs a body-attached unit in communication with a separate analysis computer. Another topology embodying the invention employs a single self-contained unit attached to the body below the head performing all data collection, signal processing and analysis functions.

Scientists studying the brain have found that EEG or brainwave signals include a number of components, including signals resulting from rhythmic activity falling within a number of frequency bands. Generally accepted terminology for signals within these various frequency bands includes delta (up to 3 Hz), theta (4 Hz to 8 Hz), alpha (8 Hz to 12 Hz), beta (12 Hz to about 30 Hz), and gamma (approximately 26 Hz to 100 Hz). Although these different brainwave signals are produced simultaneously and in combination, the frequency band within which signals are dominant (strongest) at any point in time is an indication of the state of consciousness of a person, or of the physiological state of the person. As examples, during sleep, the brain produces dominant slow delta waves with a frequency range up to 3 Hz. These tend to be the highest in amplitude and are the slowest waves. Theta waves in the frequency range from 4 Hz to 8 Hz are commonly associated with daydreaming or being in the twilight of sleep or drowsiness. Alpha waves in the frequency range from 8 Hz to 12 Hz are indicative of relaxation. Beta waves in the frequency range from 12 Hz to about 30 Hz are associated with active thinking or alertness. Gamma waves in the frequency range approximately 26 Hz to 100 Hz are theorized to represent cohesiveness of different populations of neurons working together to form a network for the purpose of carrying out a certain cognitive or motor function. Because of the filtering properties of the skull and scalp, gamma waves can only be recorded using electrodes placed directly on the exposed surface of the brain, an invasive procedure known as electrocorticography (ECoG) which requires a craniotomy.

By way of example and not limitation, EEG-based biofeedback may be employed in attention training, as is disclosed for example in Freer U.S. Pat. No. 6,097,981 titled "Electroencephalograph Based Biofeedback System And Method," and in Freer U.S. Pat. Nos. 6,402,520 and 6,626,676 titled "Electroencephalograph Based Biofeedback System For Improving Learning Skills." Again by way of example and not limitation, Freer U.S. Pat. No. 6,097,981 discloses detecting the energy levels corresponding to the alpha, beta, and theta frequency bands as an indication of the attention level of the user. In the system disclosed in U.S. Pat. No. 6,097,981, bandpass filters are employed to separate the various bands of brainwave activity, followed by RMS-to-DC converters to detect the magnitude of brainwave activity within each band of interest.

Prior to the present invention, signal acquisition for monitoring electrical activity within the brain has been strictly limited to the use of electrodes attached to the human head, and typically to the scalp, for a variety of perceived reasons. Presented hereinbelow, following description of specific embodiments with reference to drawing FIGURES, is a discussion of reasons why EEG signal acquisition has heretofore been limited to electrodes attached to the head. Likewise discussed is the manner in which embodiments of the invention effectively function to enable monitoring electrical activity within the brain of a person employing electrodes or other sensors connected or placed proximate to portions of the body below the head. Those discussions are based on the inventors' understanding and are believed to be accurate, but are not intended to limit the scope of the invention in the event a different understanding is reached.

Electrode placement on the head is limiting for a variety of reasons. As one example, if a person is active in a sport or movement, electrical activity within the brain cannot be accurately monitored using head-bound EEG electrodes because the movement of the head during the activity interferes with the signal acquisition itself by creating artifacts. Moving electrodes can disrupt signal input/output. Also, if a person has a head injury or traumatic brain injury (TBI), that person may not be able to withstand sensors placed on the head due to tissue damage.

Many people do not like the obtrusive headsets, gels, ear clips, etc. typically employed with a headset acquisition device and this has limited EEG's use in many different fields of endeavor. Helmets, hats, skull caps, headbands, eyeglasses, earphones, headphones, etc. that incorporate traditional wired EEG acquisition sensors have made EEG use somewhat prohibitive in the consumer marketplace because they reinforce a negative science fiction stereotype that connotes an intimidating or frightening effect attributable to visible wires attached to the head.

The apparatus disclosed herein in detail is particularly useful in the fields of attention training employing EEG-based biofeedback, human performance training (HPT) employing EEG-based biofeedback, gaming employing EEG-based biofeedback, and relaxation training employing EEG-based biofeedback. However, such are by way of example only, and not limitation. Accordingly, embodiments of the invention may be employed to acquire and analyze signals based on electrical activity within the brain of a person for a wide variety of purposes. Specific examples of EEG-based biofeedback employed in attention training and in computerized training apparatus are disclosed in Freer U.S. Pat. No. 6,097,981 titled "Electroencephalograph Based Biofeedback System and Method;" in Freer U.S. Pat. Nos. 6,402,520 and 6,626,676 titled "Electroencephalograph Based Biofeedback System For Improving Learning Skills;" and in Freer et al Patent Application Pub. No. US 2004/0230549 titled "Systems and Methods for Behavioral Modification and Behavioral Task Training Integrated with Biofeedback and Cognitive Skills Training." Specific examples of EEG-based biofeedback employed in human performance training are disclosed in Freer et al U.S. patent application Ser. No. 12/112,528, filed Apr. 30, 2008, published as Patent Application Pub. No. US 2008/0275358, and titled "Training Method and Apparatus Employing Brainwave Monitoring."

Referring now to FIG. 1, representative apparatus 20 embodying the invention includes a body-attachment device 22 which structurally supports an amplifier and wireless transmitter unit 24 and sensors 26 and 28 connected to the unit 24, as well as a ground electrode 30 or reference electrode 30. In FIG. 1, the sensors 26 and 28 are active electrodes 26 and 28 representative of sensors in general, including "dry" electrodes which do not require a conductive gel or paste, as well as what are known as non-contact biopotential sensors or contactless biopotential sensors. As active sensors, the sensors 26 and 28 may also be referred to as non-reference sensors or non-reference electrodes.

The body-attachment device 22 is configured for attachment to a portion of a person's body below the head. Various specific embodiments thereof are described in detail hereinbelow with reference to FIGS. 4-12. Thus, during use, the sensors 26 and 28 are attached at least proximate to portions of the body of a person below the head, as is the amplifier and wireless transmitter unit 24. The sensors 26 and 28 develop raw signals including frequency components relevant to brain electrical activity ("brainwave" signals).

Included in the amplifier and wireless transmitter unit 24 is a wireless transmitter 32 and an associated antenna 34. The apparatus 20 additionally includes a corresponding wireless receiver 36 and an associated antenna 38. The wireless receiver 36 is connected to deliver signals received from the amplifier and wireless transmitter unit 24 to a programmed computing device 40 in the form of a programmed digital computer 40, such as a personal computer (PC). Among other functions, the programmed digital computer 40 performs signal processing and analysis based on raw brainwave signals developed by the sensors 26 and 28.

In the particular configuration illustrated in FIG. 1, the amplifier and wireless transmitter unit 24 includes an amplifier 50 having a pair of high-impedance inputs 52 and 54 to which the active electrodes 26 and 28 are connected through AC-coupling capacitors 56 and 58. Shielded leads (not specifically shown) may be employed. Even so, advantageously, the electrodes 26 and 28 are located near the amplifier 50, minimizing the required lead length. The ground electrode 30, if employed, is connected to circuit ground 60.

The amplifier and wireless transmitter unit 24, in addition to the amplifier 50, includes a low pass filter 62 and an analog-to-digital converter (A/D) 64 connected to the wireless transmitter 32. The low pass filter 62 serves to attenuate or minimize signal frequency components which are above a frequency band of interest and which are unrelated to electrical activity within the brain of a person. A potential frequency component unrelated to and not relevant to brain electrical activity is a signal coupled from 50 Hz or 60 Hz AC power lines. A low pass filter 62 having a cut-off frequency within the range 20 to 40 Hz is suitable. As a more particular example, the low pass filter 62 is a fifth order switched capacitor low pass filter having a cut-off frequency of 22 Hz. In the FIG. 1 embodiment, brainwave signal components of interest are well below 50 Hz or 60 Hz, and the 22 Hz low pass filter 62 is simple and effective. In applications in which frequency ranges of brainwave signal components of interest include 50 Hz or 60 Hz, a notch filter may be employed instead of the low pass filter 62.

The analog-to-digital converter 64 is a 12-bit A/D converter, and employs a sample rate of 150 Hz. The wireless transmitter 32 is included as part of and is representative of a Bluetooth® device 32 incorporating a microchip radio transceiver. Although the wireless transmitter 32 is thus a radio (RF) transmitter 32, other forms of wireless communication may as well be employed, such as infrared (IR). A suitably-programmed microcontroller 70 also is included within the amplifier and wireless transmitter unit 24. The microcontroller 70 in a conventional manner is connected to and at least in part serves the functions of the low pass filter 62, the A/D converter 64 and the Bluetooth® device 66 (connections not shown).

The various elements within the amplifier and wireless transmitter unit 24 may be implemented employing a combination of digital and analog technologies. Moreover, the amplifier and wireless transmitter unit 24 may be implemented as an "intelligent" and reprogrammable device, with the microcontroller 70 executing software to perform various functions. The Bluetooth® device 32 is capable of bidirectional data communications, facilitating modifications and adjustments of the functioning of the amplifier and wireless transmitter unit 24, such as updating "firmware."

Correspondingly, the wireless receiver 36 is included as part of and is representative of another Bluetooth® device 36 which cooperates with the Bluetooth® device 32 to form a bidirectional wireless digital communications link. The device 36 likewise incorporates a microchip radio transceiver. In a representative embodiment, the devices 32 and 36 are configured to emulate a 9600 baud serial port through which 12 bit serial data is transmitted. The serial data is transmitted as ASCII text, using base-64 encoding. Functionally, from a signal processing point of view, the periodically-sampled output of the A/D converter 64 is connected to the programmed digital computer 40. However, as a physical and practical matter, the combination of the body-attachment device 22 and the bidirectional wireless communications link effected by the Bluetooth® devices 32 and 36 permits freedom of movement.

Implemented in software within the programmed digital computer 40, employing digital signal processing (DSP) techniques, are a pair of bandpass filters, in particular, a "theta" bandpass filter 84 and a "beta" bandpass filter 86. The bandpass filters 84 and 86 are followed by respective RMS converters 88 and 90. Accordingly, brainwave signals are bandpass-filtered and processed to determine signal magnitude within the "theta" frequency range 4 Hz to 8 Hz and within the "beta" frequency range 12 Hz to 16 Hz. In the illustrated embodiment, the output of each of the RMS converters 88 and 90 is a 10-bit binary number within the range (decimal) 0 to 1023.

As a non-limiting representation of further signal processing, a pair of threshold detectors 92 and 94 follow the RMS converters 88 and 90, respectively, to produce attention-indicating and alertness signals. Theta waves (4 Hz to 8 Hz) are particularly useful for this particular function (attention indication). A decrease in the magnitude of theta waves is indicative of less daydreaming and an increasing level of attention. In addition, an increase in the magnitude of beta waves (12 Hz to 16 Hz) indicates increasing alertness. In applications where it is desired to determine whether a person is in an attentional state, a decrease in theta wave (4 Hz to 8 Hz) activity in combination with (e.g. in ratio to) beta wave (12 Hz to 16 Hz) activity can be employed as an indicator of attention. A variety of other signal processing and analysis strategies, including analysis of delta, theta, alpha and beta wave activity, can be employed to indicate various physiological states in general of a person, including but not limited to level of attention.

Figure 12:
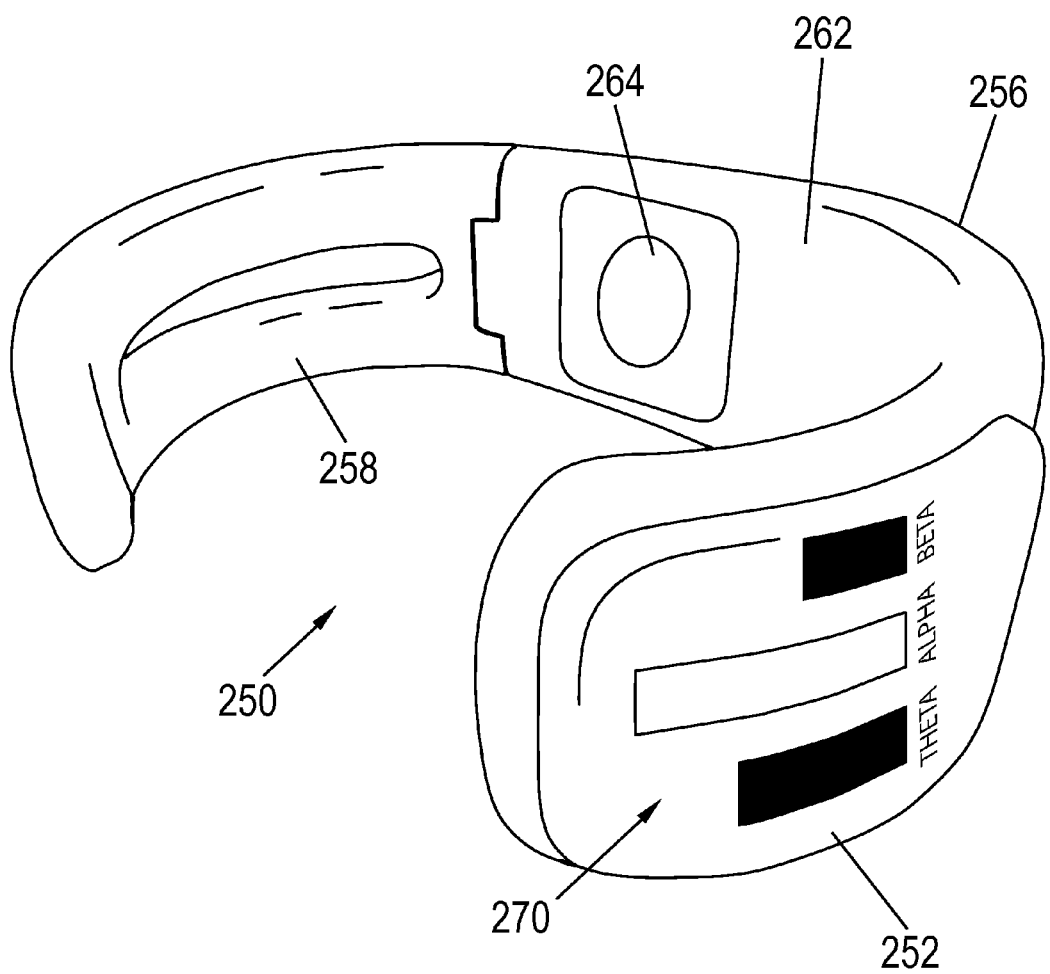
FIG. 12 illustrates the cuff of FIG. 11 in isolation.

It will be appreciated that the functions represented in FIG. 1 can be distributed in various ways, that is, allocated between the body-attached amplifier and wireless transmitter unit 24 and the programmed digital computer 40. More or fewer functions can be served by the amplifier and wireless transmitter unit 24. The digital communications link effected by the Bluetooth® devices 32 and 36 can be at different locations within the overall signal processing and analysis path. Moreover, as illustrated in FIG. 12, described hereinbelow, all of the signal processing and analysis functions can be effected within a body-attached unit.

Figure 2:
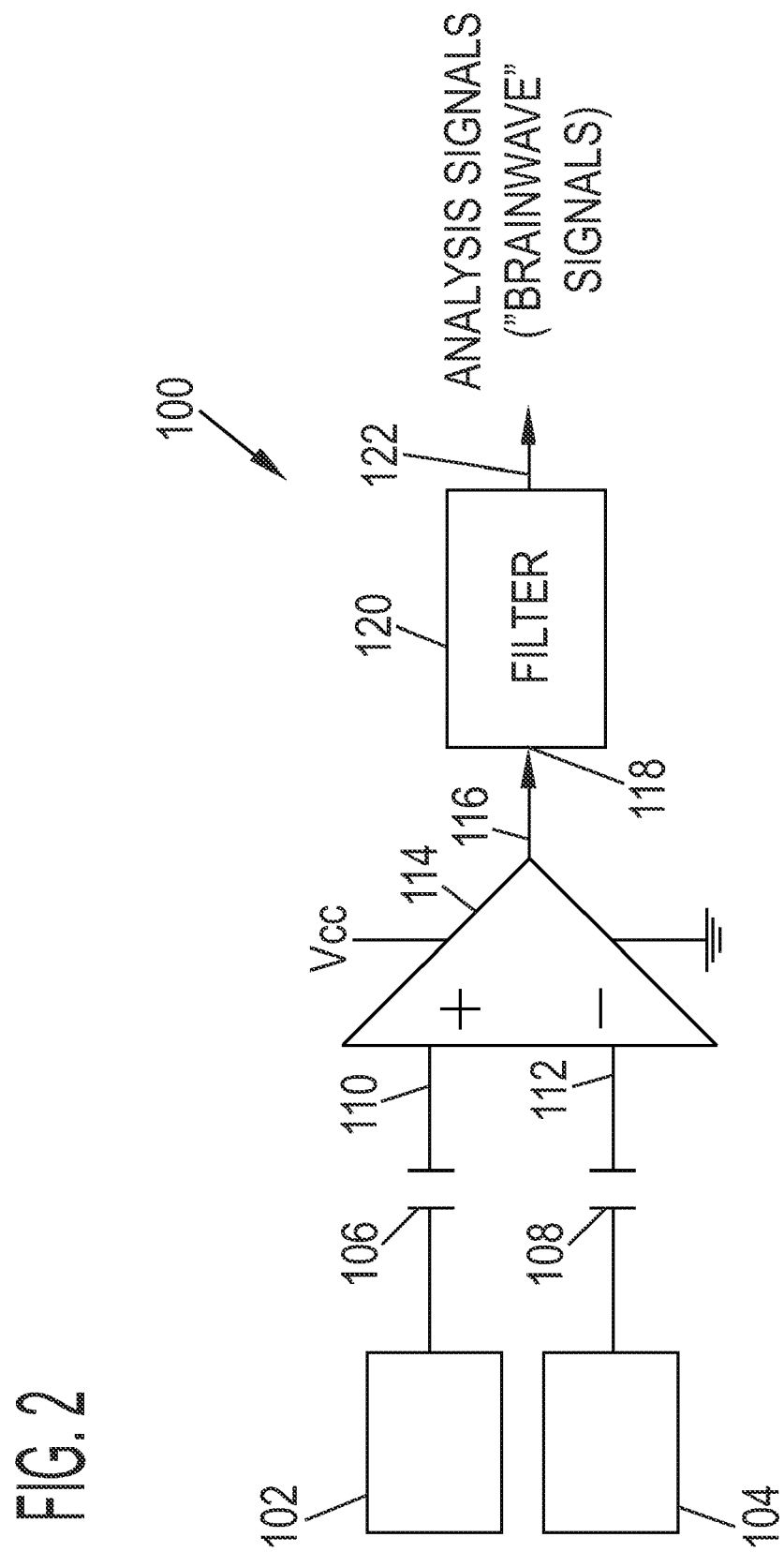
FIG. 2 is a schematic representation of another apparatus embodying the invention.

Accordingly, FIG. 2 is a representation of a generalized apparatus 100 which produces analysis signals including frequency components relevant to brain electrical activity. The FIG. 2 apparatus 100 again employs two representative sensors 102 and 104 such as active electrodes 102 and 104 connected through capacitors 106 and 108 to high impedance inputs 110 and 112 of an amplifier 114. At least the sensors 102 and 104 are positioned at least proximate to portions of the body of a person below the head to develop raw signals. The amplifier 114 has an output 116 connected to an input 118 of a filter 120. The signal processing in FIG. 2 can be analog, digital, or a combination.

The filter 120 attenuates frequency components which are unrelated to frequency components of interest and which are not relevant to brain electrical activity. Produced at an output 122 of the filter 120 are what may be termed analysis signals for further processing and analysis, the analysis signals including frequency components relevant to brain electrical activity. As described hereinabove with reference to the low pass filter 62 of FIG. 1, the FIG. 2 filter 120 can be a low pass filter or a notch filter, as examples. The selection and design of the filter 120 depend on the frequency components of interest relevant to brain electrical activity, as well as on particular unrelated frequency components which are anticipated. The filter 120 may be implemented employing digital signal processing (DSP) techniques, and may be adaptive.

The "brainwave" signals at the output 122 of the low pass filter 120 may be employed for a variety of purposes. As described hereinabove, the signals at the output 122 are analysis signals which include frequency components relevant to brain electrical activity, with unrelated frequency components attenuated. What is significant is that at least the sensors 102 and 104 are positioned at least proximate to portions of the body of a person below the head to develop raw signals.

When frequency components relevant to brain electrical activity in general are of interest, particularly when frequency components including delta waves (up to 3 Hz) are of interest, signal components corresponding to a person's heartbeat (approximately 1 Hz to 2 Hz) are unrelated frequency components of particular concern. Unrelated frequency components corresponding to electrical activity of a person's heart are particularly high in magnitude when sensors are connected to portions of the body below the head. The invention may be embodied in systems in which signal components in the raw signals resulting from electrical activity of a person's heart are actively attenuated. In an ideal case, signal components resulting from electrical activity of a person's heart are entirely cancelled, in what may be referred to and is known as active cancellation.

Figure 3:
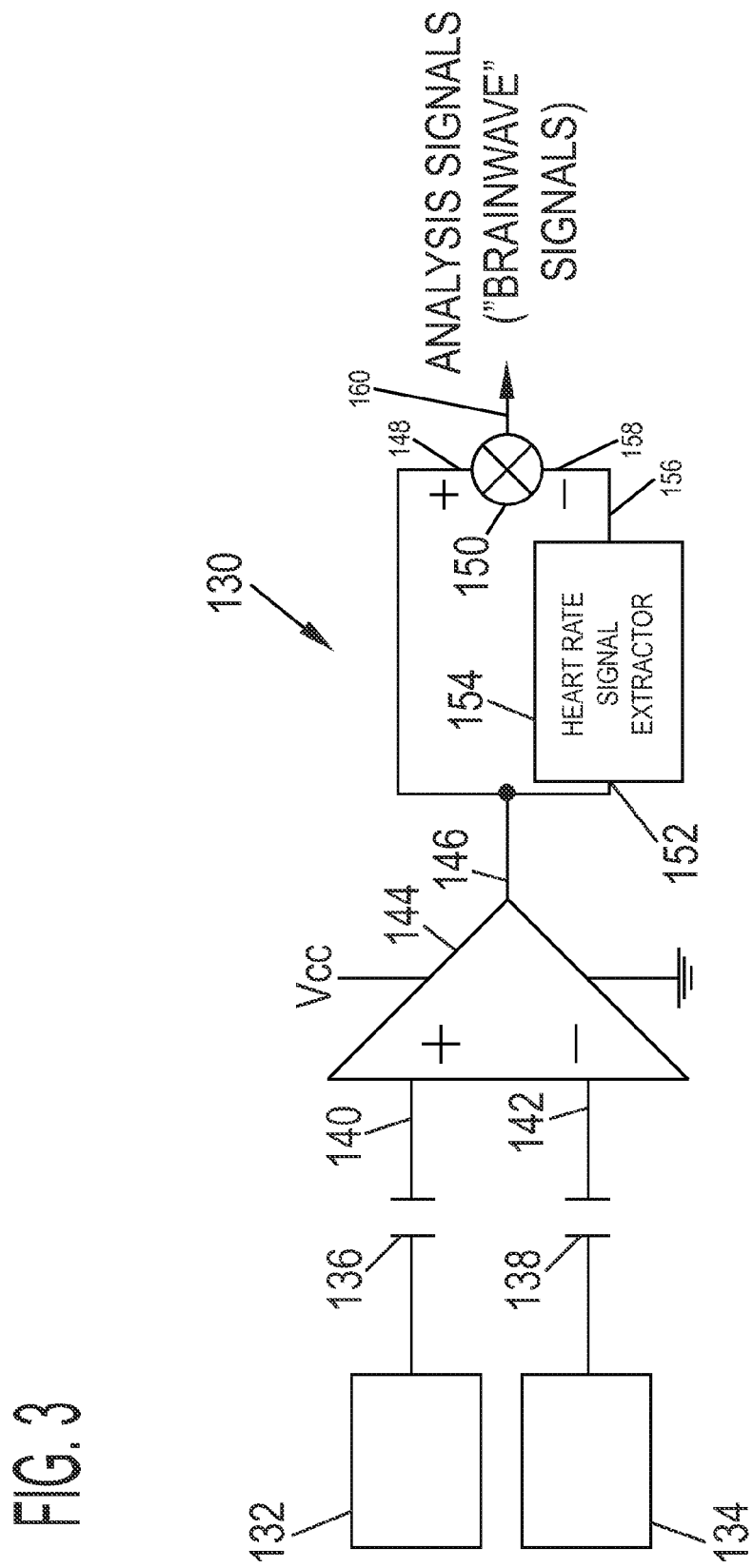
FIG. 3 is a schematic representation of yet another apparatus embodying the invention.

FIG. 3 is a representation of a generalized apparatus 130 which employs such active attenuation to produce analysis signals including frequency components relevant to brain electrical activity. The FIG. 3 apparatus 130 again employs two representative sensors 132 and 134 such as active electrodes 132 and 134 connected through capacitors 136 and 138 to high impedance inputs 140 and 142 of an amplifier 144. At least the sensors 132 and 134 are positioned at least proximate to portions of the body of a person below the head to develop raw signals.

The FIG. 3 amplifier 144 has an output 146 connected to two signal branches. One branch is connected to a (+) input 148 of a summing junction 150, and the other to an input 152 of a heart rate signal extractor 154 which extracts signal components resulting from electrical activity of a person's heart. An output 156 of the heart rate signal extractor 154 is connected to a (−) input 158 of the summing junction 150. Analysis signals which include frequency components relevant to brain electrical activity with unrelated frequency components attenuated, are produced at the output 160 of the summing junction 150.

Thus, within the summing junction 150, signal components resulting from electrical activity of a person's heart are actively attenuated. Again, in an ideal case, signal components resulting from electrical activity of a person's heart are entirely cancelled, in what may be referred to and is known as active cancellation.

Heart rate monitors are well known, which recognize and track a person's heartbeat or heart rate, typically presenting a digital display. The heart rate signal extractor 154 employs digital signal processing (DSP) techniques to recognize, isolate and track signal components resulting from electrical activity of a person's heart. The thus-recognized, isolated and tracked signal is provided as an output of the heart rate signal extractor 154. With appropriate magnitude adjustment, the frequency or signal components resulting from electrical activity of a person's heart but unrelated to brainwave activity of interest are attenuated, or stated alternatively, at least in part cancelled.

Again, the "brainwave" signals at the output 160 of the summing junction 150 may be employed for a variety of purposes. The signals at the output 160 are analysis signals, which include frequency components relevant to brain electrical activity, with unrelated frequency components attenuated. Again, what is significant is that at least the sensors 132 and 134 are positioned at least proximate to portions of the body of a person below the head to develop raw signals.

As an alternative to the heart rate signal extractor 154 and summing junction of FIG. 3, the topology of FIG. 2 may be employed to provide similar functionality. More particularly, the FIG. 2 filter 120 may be an adaptive DSP filter programmed to attenuate signal components resulting from electrical activity of a person's heart, as well as other signals (such as coupled 50 Hz or 60 Hz AC power line signals) unrelated and not relevant to brain electrical activity.

Signal components resulting from electrical activity of a person's heart can be used for at least two other purposes in embodiments of the invention.

One such other purpose is to ensure that a body attachment device and, in particular, sensors 26 and 28, 102 and 104, or 132 and 134 are in fact attached to, in contact with, or otherwise functionally proximate the body of a person, for convenience collectively referred to in this paragraph as "presence." Ensuring such presence can be employed to ensure that sensed signal components within a brainwave frequency band are in fact representative of brainwaves and are not the result of stray signals coupled from environmental sources, in other words to validate that an EEG signal is being collected. Ensuring such presence can also be employed to conserve battery life, by entering a low-power "standby" mode when the absence of signal components resulting from electrical activity of a person's heart indicates no presence.

Another such other purpose is to combine indications resulting from brain electrical activity (i.e. EEG) and from electrical activity of a person's heart (i.e. EKG) for a more comprehensive analysis and indication of a person's cognitive and physiological state. Embodiments of the invention thus provide the foundation for a dual technology approach (EEG and EKG) for more comprehensive physiological state monitoring.

FIGS. 4-7 illustrate a body-attachment device 170 embodying the invention corresponding to the FIG. 1 body-attachment device 22, as well as an amplifier and wireless transmitter unit 172 corresponding to the FIG. 1 amplifier and wireless transmitter unit 24. The amplifier and wireless transmitter unit 172 includes internal components, including a battery (not shown), as described hereinabove with reference to the amplifier and wireless transmitter unit 24 of FIG. 1.

Figure 4:
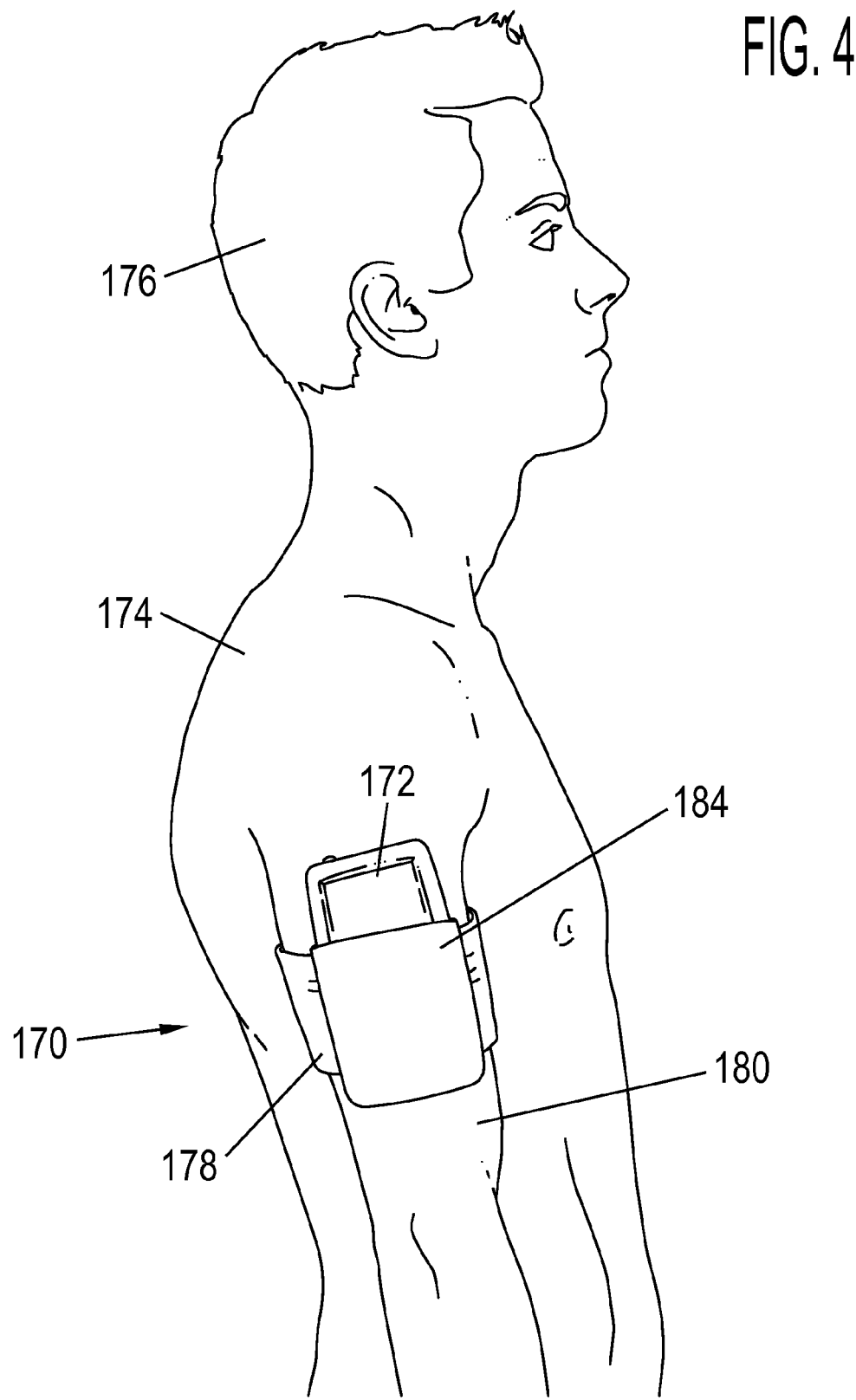
FIG. 4 illustrates an amplifier and wireless transmitter unit and a body-attachment device embodying the invention attached to an upper arm of a person.
Figure 5:
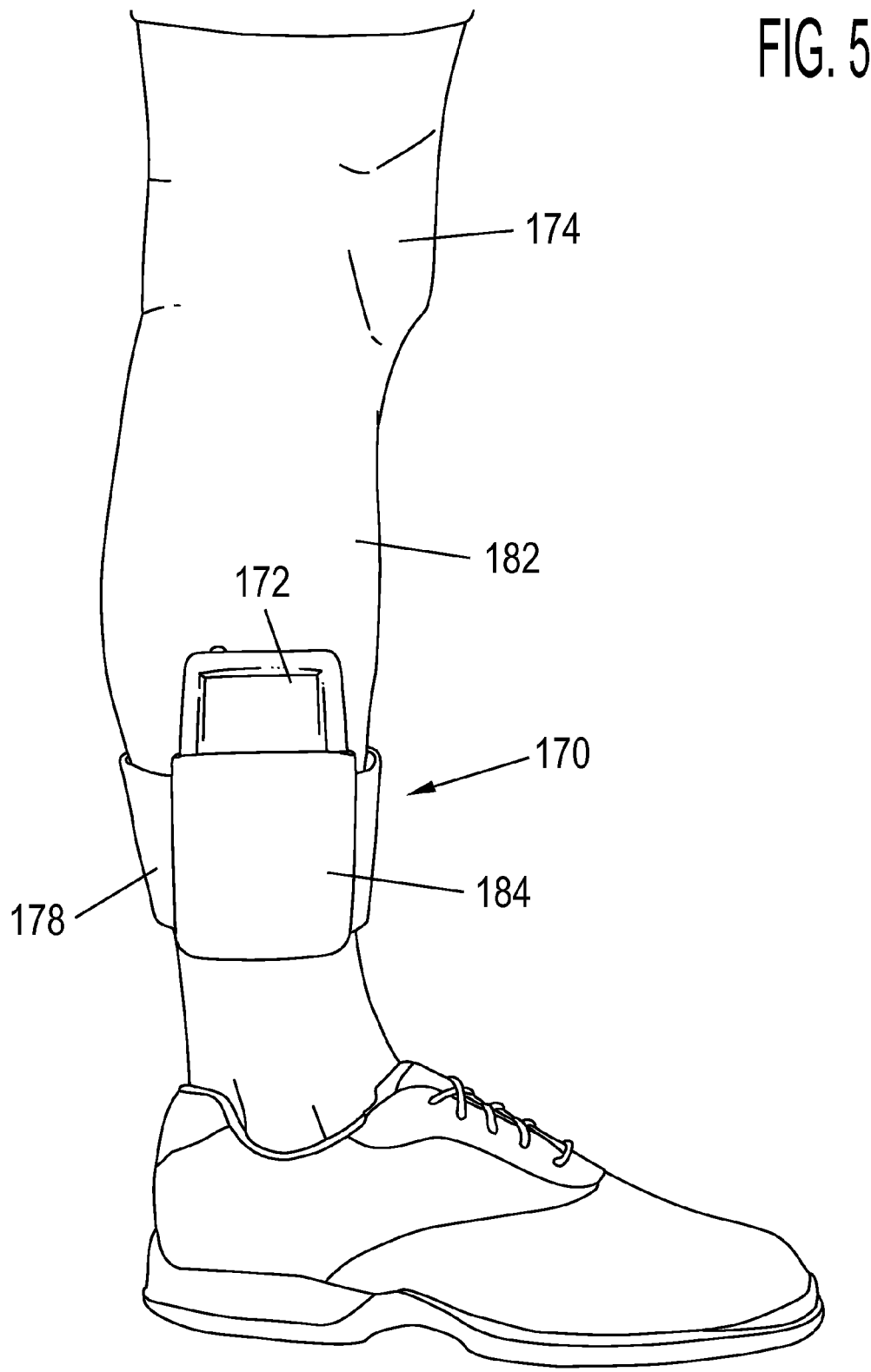
FIG. 5 illustrates the unit and the body-attachment device of FIG. 4 attached to a lower leg of a person.
Figure 6:
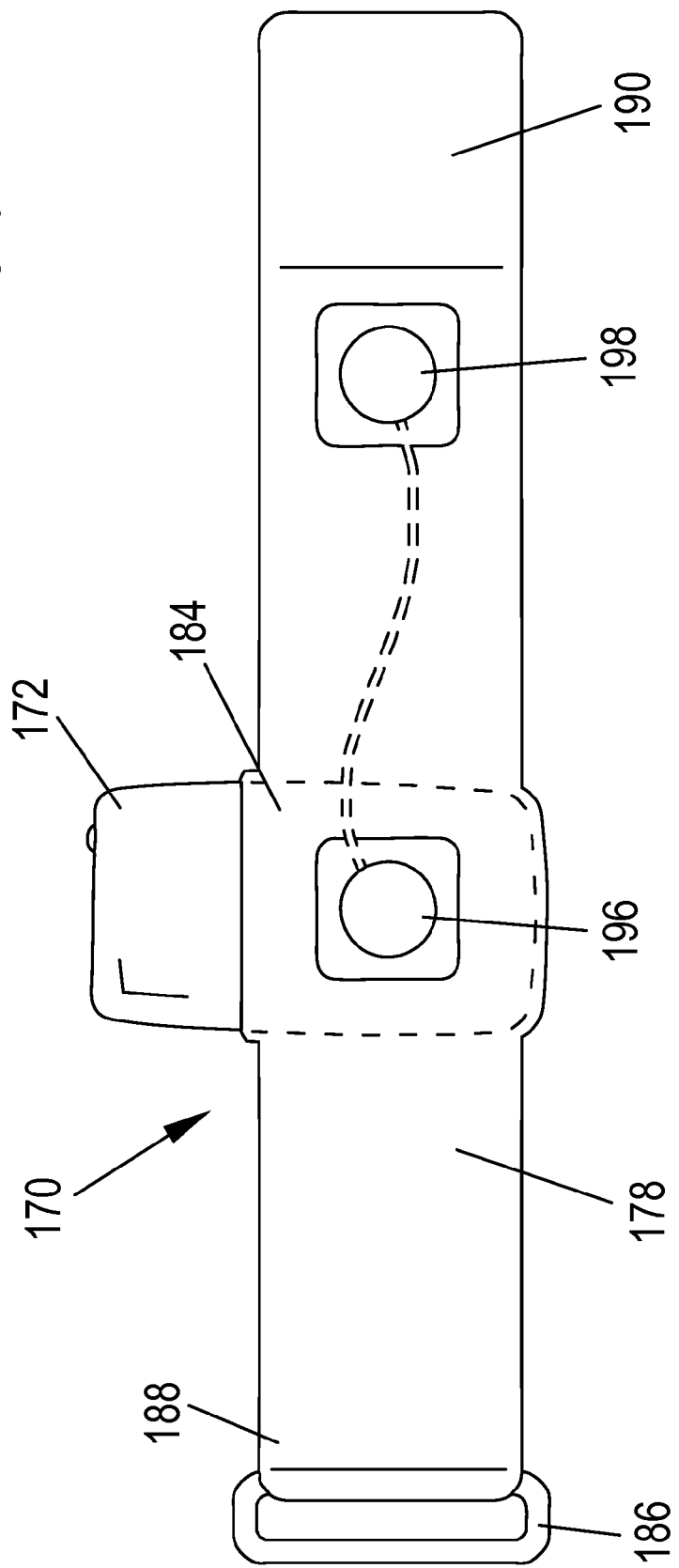
FIG. 6 illustrates the unit and the body-attachment device of FIGS. 4 and 5 spread out and unattached.

A person 174 is represented in FIGS. 4 and 5. The body-attachment device 170 of FIGS. 4-7 is configured for attachment to a portion of the body of the person 174 below the head 176. The body-attachment device 170 provides structural support for the amplifier and wireless transmitter unit 172, and more particularly takes the form of an adjustable band 178 configured for attachment to an arm 180 (FIG. 4) or a leg 182 (FIG. 5) of the person 174. A pocket 184 for the amplifier and wireless transmitter unit 172 is included.

Figure 7:
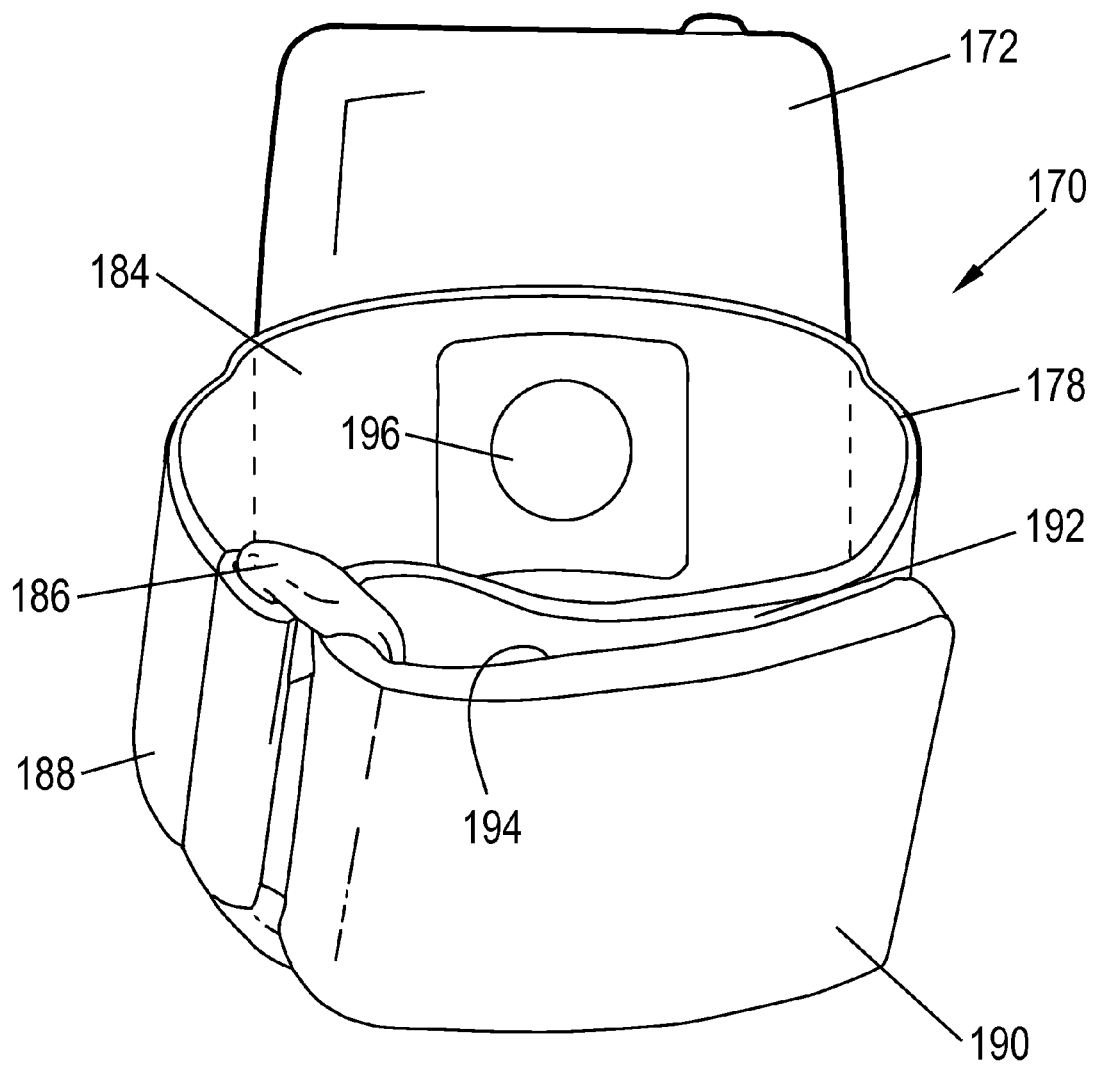
FIG. 7 illustrates the unit the body-attachment device of FIGS. 4 and 5 in the buckled configuration as worn.

The adjustable band 178 includes an apertured link 186 (FIGS. 6 and 7) secured to one end 188 thereof. During use, the other end 190 of the band 178 is passed through the apertured link 186, folded back on itself, and secured by hook-and-loop fastener elements 192 and 194 as illustrated in FIG. 7.

Also supported by the adjustable band 178 are a pair of sensors 196 and 198 corresponding to the sensors 26 and 28 described hereinabove with reference to FIG. 1. The sensors 196 and 198 are electrically connected to the amplifier and wireless transmitter unit 172, and operate as described hereinabove with reference to FIG. 1.

The sensors 196 and 198 thus, during use, are attached at least proximate to a portion of the person's 174 body below the head, such as the arm 180 (FIG. 4) or leg 182 (FIG. 5).

It will be appreciated that the programmed digital computer 40 and wireless receiver 36 or Bluetooth® device 36 of FIG. 1 are employed in connection with the embodiment of FIGS. 4-7, and function as described hereinabove with reference to FIG. 1.

Figure 8:
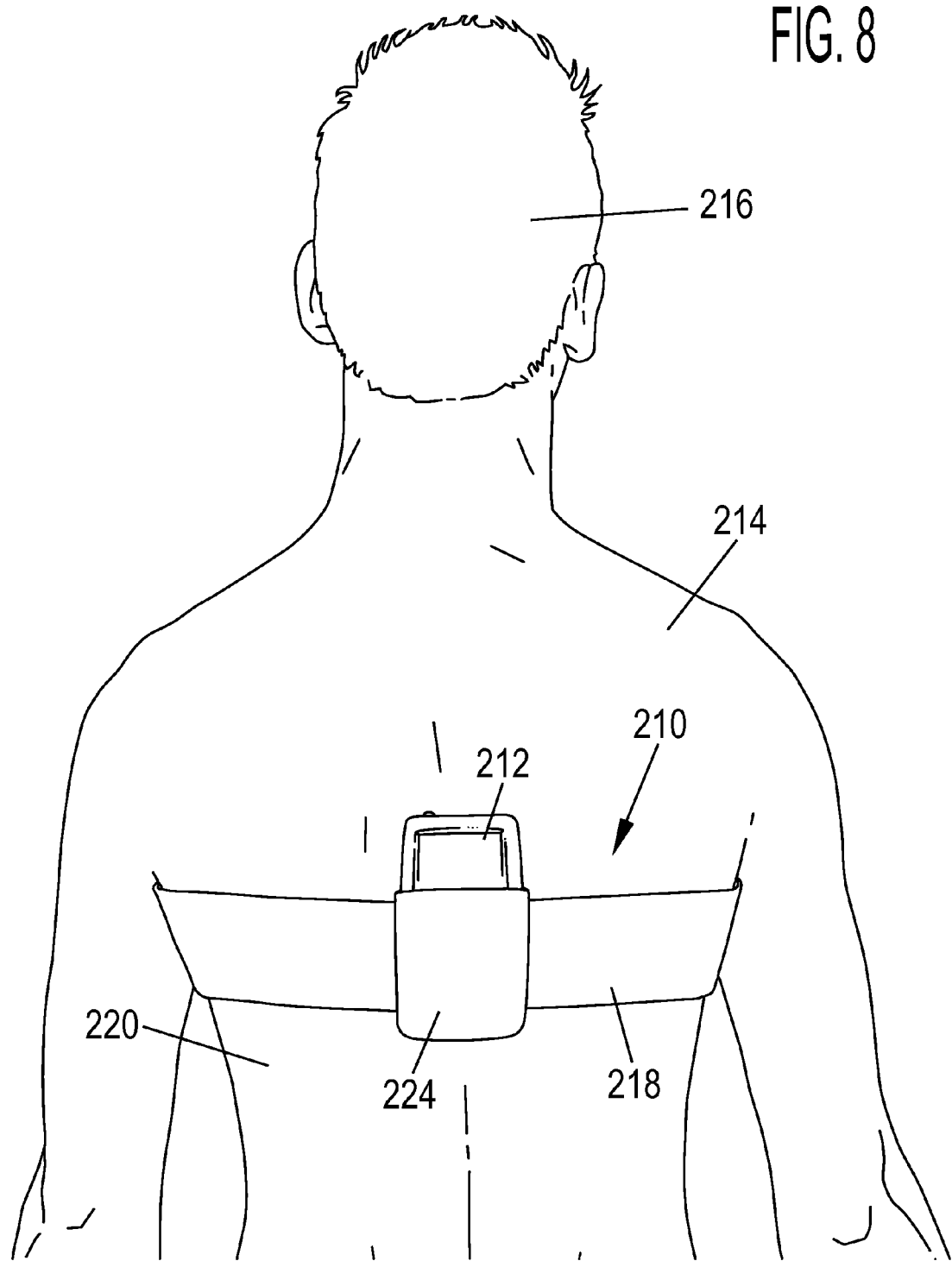
FIG. 8 illustrates an amplifier and wireless transmitter unit and another body-attachment device embodying the invention, attached to the back of a person.
Figure 9:
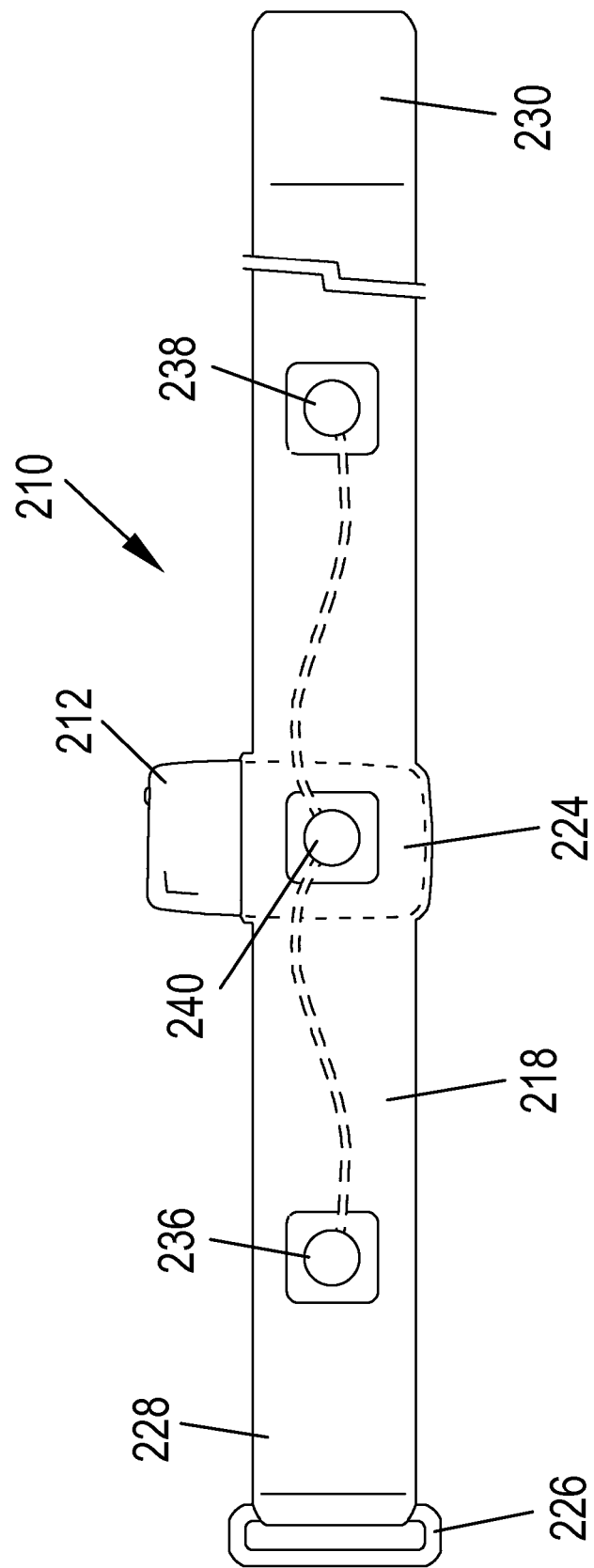
FIG. 9 illustrates the unit and body-attachment device of FIG. 8 with the adjustable band portion thereof laid out flat.
Figure 10:
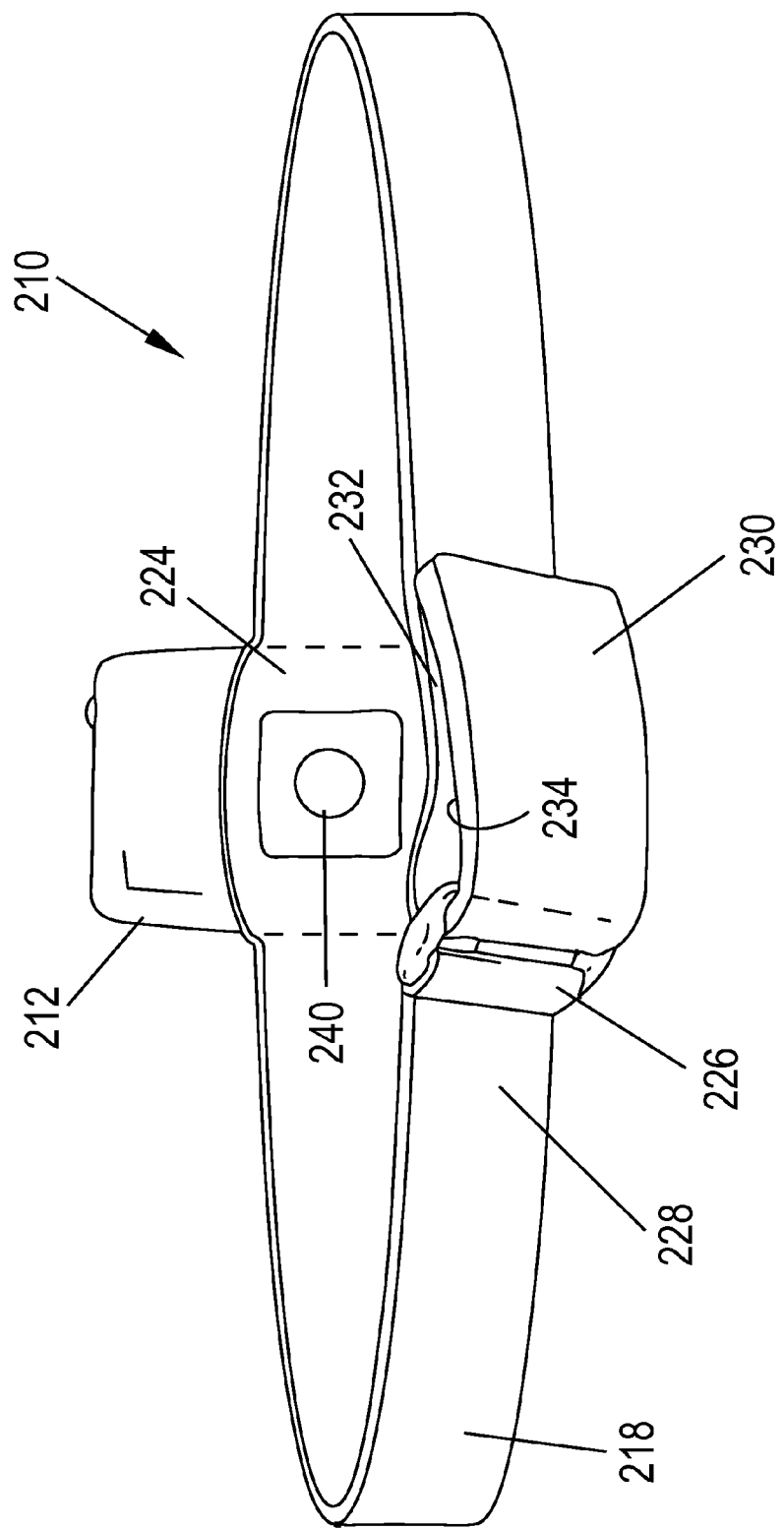
FIG. 10 illustrates the unit and body-attachment device of FIG. 8 buckled in the same configuration as when worn.

FIGS. 8-10 illustrate another body-attachment device 210 embodying the invention corresponding to the FIG. 1 body-attachment device 22, as well as an amplifier and wireless transmitter unit 212 corresponding to the FIG. 1 amplifier and wireless transmitter unit 24. The amplifier and wireless transmitter unit 212 includes internal components, including a battery (not shown), as described hereinabove with reference to the amplifier and wireless transmitter unit 24 of FIG. 1.

A person 214 is represented in FIG. 8. The body-attachment device 210 of FIGS. 8-10 is configured for attachment to a portion of the body of the person 214 below the head 216. The body-attachment device 210 provides structural support for the amplifier and wireless transmitter unit 212, and more particularly takes the form of an adjustable band 218 configured for attachment around the torso 220 of the person 214. A pocket 224 for the amplifier and wireless transmitter unit 212 is included.

The adjustable band 218 includes an apertured link 226 (FIGS. 9 and 10) secured to one end 228 thereof. During use, the other end 230 of the band 218 is passed through the apertured link 226, folded back on itself, and secured by hook-and-loop fastener elements 232 and 234 as illustrated in FIG. 10. The amplifier and wireless transmitter unit 212 is positioned at the back of the person 214 during use.

Also supported by the adjustable band 218 are a pair of active sensors 236 and 238 corresponding to the sensors 26 and 28 described hereinabove with reference to FIG. 1, as well as a ground electrode 240 corresponding to the FIG. 1 ground electrode 30. The sensors 236 and 238 are electrically connected to the amplifier and wireless transmitter unit 212, and operate as described hereinabove with reference to FIG. 1.

The sensors 236 and 238 thus, during use, are attached at least proximate to a portion of the person's 214 body below the head, such as the torso 220.

It will be appreciated that the programmed digital computer 40 and wireless receiver 36 or Bluetooth® device 36 of FIG. 1 are employed in connection with the embodiment of FIGS. 8-10, and function as described hereinabove with reference to FIG. 1.

Figure 11:
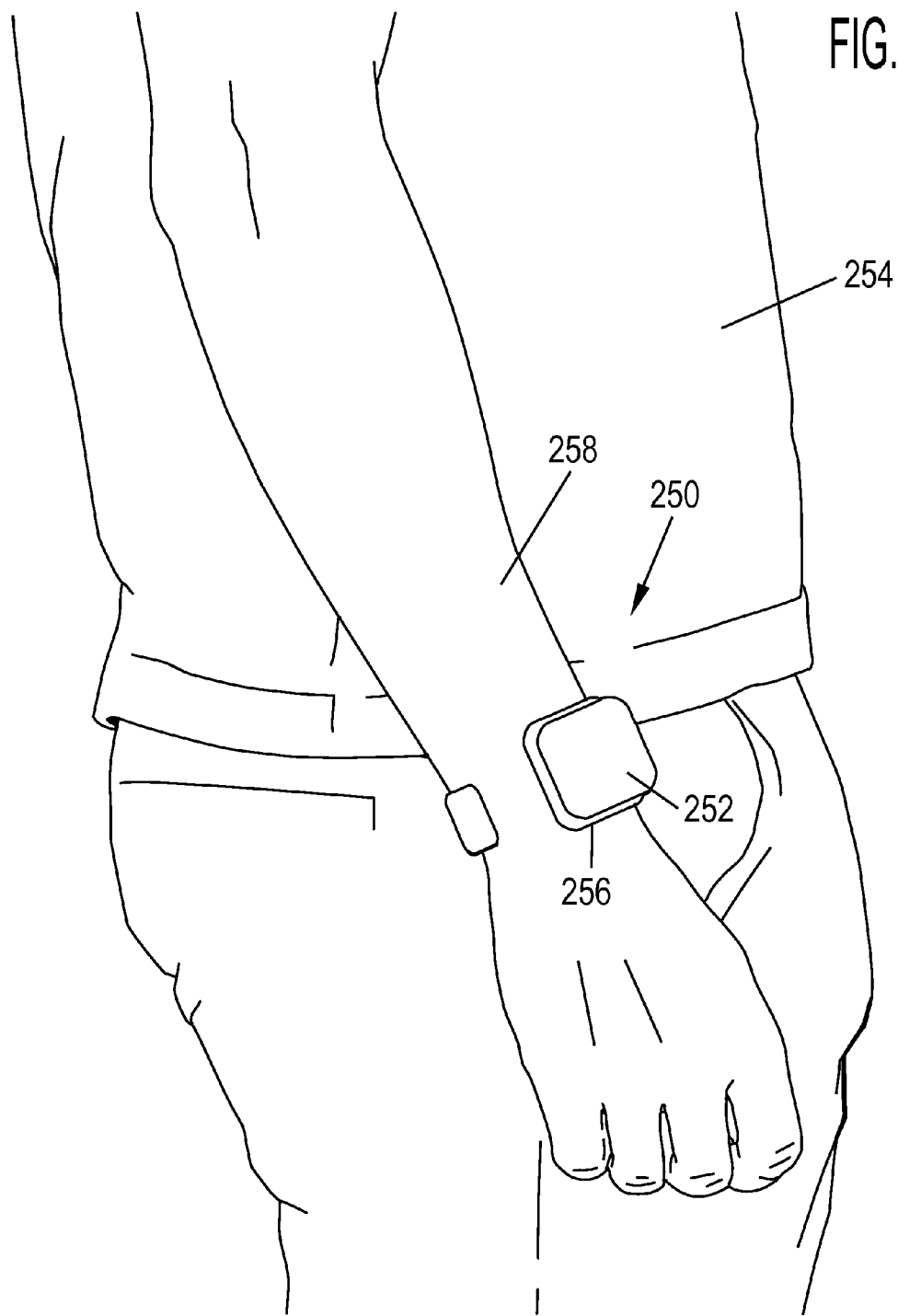
FIG. 11 illustrates an amplifier and wireless transmitter unit in another body-attachment device embodying the invention in the form of a cuff attached to an arm of a person, near the wrist.

FIGS. 11 and 12 illustrate yet another body-attachment device 250 embodying the invention corresponding to the FIG. 1 body-attachment device 22, as well as an amplifier and wireless transmitter unit 252 corresponding to the FIG. 1 amplifier and wireless transmitter unit 24. The amplifier and wireless transmitter unit 252 includes internal components, including a battery (not shown), as described hereinabove with reference to the amplifier and wireless transmitter unit 24 of FIG. 1.

A person 254 is represented in FIG. 11. The body-attachment device 250 of FIGS. 11 and 12 is configured for attachment to a portion of the body of the person 254 below the head. The body-attachment device 250 provides structural support for the amplifier and wireless transmitter unit 252, and more particularly takes the form of a cuff 256 configured for attachment to an arm 258 (FIG. 11) or a leg (not shown) of the person 254. To facilitate attachment and removal, the cuff 256 includes a hinged end piece 260, which is either spring loaded or equipped with a locking mechanism.

The amplifier and wireless transmitter unit 252 is either an integral part of the cuff 256, or a detachable element. On the inside surface 262 of the cuff 256 are a pair of sensors corresponding to the sensors 26 and 28 described hereinabove with reference to FIG. 1. In FIG. 12, only one sensor 264 is visible. The other sensor is located on the inside surface 262 at the general position of the amplifier and wireless transmitter unit 252. The sensors including the sensor 264 are electrically connected to the amplifier and wireless transmitter unit 252, and operate as described hereinabove with reference to FIG. 1.

The sensors including the sensor 264 thus, during use, are attached at least proximate to a portion of the person's 254 body below the head, such as the arm 258 (FIG. 12).

It will be appreciated that the programmed digital computer 40 and wireless receiver 36 or Bluetooth® device 36 of FIG. 1 are employed in connection with the embodiment of FIGS. 11 and 12, and function as described hereinabove with reference to FIG. 1.

FIG. 12 in addition illustrates an alternative embodiment wherein all data collection, signal processing and analysis functions are implemented in a single self-contained unit attached to the body below the head. As represented by a bar graph display 270 in FIG. 12, signal processing may be employed to determine and drive a display representing the magnitude of brainwave activity in different brainwave frequency bands of interest. In FIG. 12, the bar graph display 270 represents the magnitude of brainwave activity in the "theta," "alpha" and "beta" frequency bands. Alternatively, a single display of a person's level of attention can be provided. In either case, auditory signaling may also be employed to indicate when certain pre-programmed thresholds have been either exceeded or unattained, thus alerting the user that physiological change is necessary.

A foremost perceived reason why EEG signal acquisition heretofore has been limited to electrodes attached to the head is that EEG signals are miniscule with poor spatial resolution. Past EEG devices are particularly sensitive only to post-synaptic potentials generated in superficial layers of the cortex. EEG signals are actually the result of millions of electro-chemical pulses of energy fired across the synapse or minute divide between brain cells (neurons). The energy resulting from this process is very small and is measured in microvolts. Because the signal is incredibly minute, signal acquisition from anywhere other than the head has been considered to not be feasible.

Spatially, EEG sensors detect signals from the crests of gyri directly abutting the skull (the shortest distance between the two points) and radial to the skull. Energy produced from synapses located far deeper in the cortex, inside deep fissures (sulci), are in midline or deep structures such as the hippocampus, or produce currents which are tangential to the skull only very nominally contribute to the EEG signal.

Another perceived reason why EEG signal acquisition heretofore has been limited to electrodes attached to the head is that the meninges (collective term for the three membranes covering the brain and spinal cord), cerebrospinal fluid, skull, and oils in the skin tend to obstruct and diffuse the EEG signal, obscuring its intracranial source. Conductive gels or special dry sensors conventionally are used to obtain EEG signals and overcome natural impedance, but such conductive gels or special dry sensors cannot eliminate the interference or obstruction caused by the meninges, cerebrospinal fluid, and skull.

Yet another perceived reason why EEG signal acquisition heretofore has been limited to electrodes attached to the head is that it is mathematically impossible to reconstruct a unique intracranial current source for a given EEG signal, because some currents produce potentials that cancel each other out. This is referred to as the inverse problem.

As a result, as current and conventional practice, EEG signals are acquired or taken only from the head, either on the scalp itself, or via electrodes attached to the ears.

Employing radio signal reception as a loose analogy or example, as one moves away from a radio transmitting antenna or a tower and towards the country, the signal not only weakens, but many more interfering factors arise like competing radio signals from neighboring stations, industrial noise, and physical obstructions.

Even so, it has been discovered that sensors attached to portions of the body below the head develop raw signals which, when amplified and filtered as described hereinabove, provide useful analysis signals for monitoring electrical activity within the brain. Particularly useful and effective are embodiments wherein raw signals from the electrodes or sensors are filtered and analyzed to determine the magnitude of brainwave activity within particular frequency bands of interest which are indicative of level of attention. Stated in other words, it has been discovered that attentional brainwave monitors which include electrodes intended to be attached to the head are also effective when the electrodes (or other sensors such as non-contact bio-sensors) are attached, for example, to the arms.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. Apparatus for monitoring electrical activity within the brain of a person having a body including a head, said apparatus comprising:
   a sensor;
   a unit including at least an amplifier connected for receiving signals from said sensor;
   a body-attachment device configured for attachment to a portion of the person's body below the head, said body-attachment device providing structural support for said sensor and for said unit, and said body-attachment device positioning said sensor at least proximate to the skin of the body of the person with the exception of the head; and
   a programmed computing device receiving signals from said amplifier;
   said unit and said computing device functioning together to isolate and analyze frequency components of the signals relevant to brain electrical activity while attenuating unrelated frequency components.

2. The apparatus of claim 1, wherein said body-attachment device comprises an adjustable band configured for attachment to an arm or leg of the person.

3. The apparatus of claim 1, wherein said body-attachment device comprises an adjustable band configured for attachment around the torso of the person.

4. The apparatus of claim 1, wherein said body-attachment device comprises a cuff configured for attachment to an arm or leg of the person.

5. The apparatus of claim 1, wherein said unit and said computing device function together to produce at least one bandpass-filtered attention-indicating signal as an indication of the person's level of attention.

6. The apparatus of claim 1, wherein:
   said unit further includes a wireless transmitter for receiving signals from said sensors and wirelessly transmitting at least a portion of the signals; said apparatus further comprising:
   a wireless receiver for receiving the transmitted portion of the signals; and wherein
   said programmed computing device is connected to said wireless receiver.

7. The apparatus of claim 1, wherein said unit includes a low pass filter.

8. The apparatus of claim 7, wherein said low pass filter has a cutoff frequency within the range of 20 Hz to 40 Hz.

9. The apparatus of claim 7, wherein said programmed computing device implements a bandpass filter to isolate frequency components of the signals within a predetermined frequency range relevant to the person's level of attention.

10. A method for monitoring EEG electrical activity within the brain of a person having a body including a head, said method comprising:
    employing the apparatus of claim 1 by positioning the sensor at least proximate to portions of the skin of the body with the exception of the head to develop raw signals; and filtering the raw signals to produce analysis signals including frequency components relevant to EEG brain electrical activity while attenuating unrelated frequency components.

11. The method of claim 10, which comprises positioning the sensor at least proximate to an arm, wrist, leg or back of the person.

12. The method of claim 10, wherein said step of filtering the raw signals comprises employing a low pass filter.

13. The method of claim 12, wherein said step of filtering the raw signals comprises employing a low pass filter having a cutoff frequency within the range of 20 Hz to 40 Hz.

14. The method of claim 10, which further comprises:
    adaptively determining heart rate signals of the person from the raw signals; and wherein
    filtering the raw signals to produce analysis signals including frequency components relevant to brain electrical activity while attenuating unrelated frequency components comprises employing the determined heart rate signals to actively cancel heart rate signal components from the raw signals.

* * * * *